(12) United States Patent
Bruggeman et al.

(10) Patent No.: US 9,808,476 B2
(45) Date of Patent: *Nov. 7, 2017

(54) FEED SUPPLEMENT COMPRISING OLIGOSACCHARIDES AND MEDIUM CHAIN FATTY ACIDS

(71) Applicant: Nutrition Sciences NV/SA, Drongen (BE)

(72) Inventors: Geert Bruggeman, Bruges (BE); Katrien Deschepper, De Pinte (BE)

(73) Assignee: NUTRITION SCIENCES NV/SA, Drongen (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/050,925

(22) Filed: Feb. 23, 2016

(65) Prior Publication Data

US 2016/0250239 A1     Sep. 1, 2016

Related U.S. Application Data

(63) Continuation of application No. 13/640,266, filed as application No. PCT/EP2011/055945 on Apr. 14, 2011, now Pat. No. 9,271,517.

(30) Foreign Application Priority Data

Apr. 14, 2010 (BE) .................................. 2010/00241

(51) Int. Cl.
| | |
|---|---|
| *A61K 31/702* | (2006.01) |
| *A61K 31/20* | (2006.01) |
| *A23K 20/158* | (2016.01) |
| *A23K 20/163* | (2016.01) |
| *A23K 50/75* | (2016.01) |
| *A23K 50/30* | (2016.01) |
| *A23K 50/60* | (2016.01) |
| *A23L 29/30* | (2016.01) |
| *A23L 33/115* | (2016.01) |
| *A23K 50/70* | (2016.01) |
| *A23K 50/80* | (2016.01) |
| *A23K 20/121* | (2016.01) |
| *A61K 9/00* | (2006.01) |
| *A61K 45/06* | (2006.01) |

(52) U.S. Cl.
CPC .......... *A61K 31/702* (2013.01); *A23K 20/121* (2016.05); *A23K 20/158* (2016.05); *A23K 20/163* (2016.05); *A23K 50/30* (2016.05); *A23K 50/60* (2016.05); *A23K 50/70* (2016.05); *A23K 50/75* (2016.05); *A23K 50/80* (2016.05); *A23L 29/30* (2016.08); *A23L 33/115* (2016.08); *A61K 9/0053* (2013.01); *A61K 31/20* (2013.01); *A61K 45/06* (2013.01); *A23V 2002/00* (2013.01)

(58) Field of Classification Search
CPC ...................................................... A61K 31/20
See application file for complete search history.

(56) References Cited

U.S. PATENT DOCUMENTS

| | | | |
|---|---|---|---|
| 4,446,165 | A | 5/1984 | Roberts |
| 4,961,934 | A | 10/1990 | Iwasaki et al. |
| 4,971,815 | A | 11/1990 | Tamatani et al. |
| 6,468,568 | B1 | 10/2002 | Leusner et al. |
| 2006/0105962 | A1 | 5/2006 | Robinson |
| 2007/0009502 | A1 | 1/2007 | Lall et al. |
| 2007/0219270 | A1 | 9/2007 | Bruggeman |
| 2008/0003330 | A1 | 1/2008 | Rueda et al. |
| 2009/0186852 | A1 | 7/2009 | Bruggeman et al. |

FOREIGN PATENT DOCUMENTS

| | | |
|---|---|---|
| CN | 101454011 A | 6/2009 |
| EP | 0089376 | 9/1983 |
| EP | 1018342 | 7/2000 |
| EP | 1314358 | 5/2003 |
| JP | 05-049410 | 3/1993 |
| JP | 2006-055145 | 3/2006 |
| WO | WO 2007/138047 A2 | 12/2007 |
| WO | WO 2009/020481 A2 | 2/2009 |

OTHER PUBLICATIONS

International Search Report dated Jul. 28, 2011, issued to priority international application No. PCT/EP2011/055945.
First Office Action issued in Chinese Patent Application No. 201180018820.8, dated Aug. 22, 2013.
Anonymous, "Fructooligosaccharide," downloaded from http://en.wikipedia.org/wiko/Oligofructose, on Oct. 8, 2012, 4 pages.
Batteteau et al. "Production of oligosaccharides as promising new food additive generation", Food Technol. Biotechnol., 2006, 44(3):323-333.
Bezard, et al. "Triglyceride Composition of Coconut Oil," Journal of the American Oil Chemists' society, vol. 48, pp. 134-139, Mar. 1, 1971.

(Continued)

*Primary Examiner* — Bin Shen
(74) *Attorney, Agent, or Firm* — Knobbe, Martens, Olson & Bear LLP

(57) ABSTRACT

The present invention relates to a feed supplement and a feed containing this feed supplement, comprising 1) a homotrimer, heterotrimer, homotetramer and/or heterotetramer of a carbohydrate component selected from the group consisting of a pentose saccharide, a hexose saccharide, glucuronic and galacturonic acid, and 2) a medium-chain fatty acid (MCFA), selected from the group consisting of caproic acid (C6), caprylic (C8), capric (C10) and lauric acid (C12). The invention also refers to the use of the feed supplement or feed in order to improve the efficiency of animal production, such as weight gain, feed conversion, nutritive value, health and wellbeing through the selective elimination of enteropathogens.

16 Claims, 1 Drawing Sheet

(56) References Cited

OTHER PUBLICATIONS

Immerseel et al. "Medium-chain Fatty Acids Decrease Colonization and Invasion Through *hilA* Suppression Shortly after Infection of Chickens with *Salmonella enterica* Scrovar Enteritidis", Applied and Environmental Microbiology, 2004, 70(6):3582-3587.

Kaunitz et al. The J of the American Oil Chemistry Society, 1958, 35:10-13.

Simpson et al. JBC, 1958, 230:457-472.

FEED SUPPLEMENT COMPRISING OLIGOSACCHARIDES AND MEDIUM CHAIN FATTY ACIDS

CROSS-REFERENCE TO RELATED APPLICATIONS

This application is a continuation of U.S. application Ser. No. 13/640,266, filed Oct. 9, 2012, now U.S. Pat. No. 9,271,517, issued Mar. 1, 2016 which is the U.S. National Phase under 35 U.S.C. §371 of International Application PCT/EP2011/055945, filed Apr. 14, 2011, which claims priority to BE 2010/00241, filed Apr. 14, 2010.

TECHNICAL FIELD

The present invention relates to a feed supplement comprising oligosaccharides and medium chain fatty acids and their use to improve the gastrointestinal ecosystem. In particular, the invention relates to the use of 1) tri- and tetra-oligosaccharides or their extracts, or derivatives thereof, or mixtures thereof, and 2) medium chain fatty acids (MCFA), salts, derivatives and mixtures thereof and where the MCFA is selected from the group consisting of caproic acid (C6), caprylic (C8), capric (C10) and lauric acid (C12), to improve the microbial ecosystem in the gastrointestinal tract of an animal by specific elimination of pathogens from the gastrointestinal tract.

BACKGROUND

In today's animal production systems there is a delicate balance between intestinal flora and its host, and disruption of this balance (by e.g. bacterial infection) has a negative impact on the overall efficiency of the animals (Eckel, 1999). Knowledge of the problems of intestinal microbial infection in animals opens the door to radically new ways of bio-regulatory processes to be influenced by nutrition concepts, the frequency reduction of diarrhoea and even mortality, by stabilizing the intestinal flora. In the past, these infection problems were partially solved by adding antibiotics to the feeds as growth stimulator.

Currently, decades after the discovery of traditional antimicrobials (e.g. penicillin), many bacteria became resistant to one, and in many cases multiple antimicrobials (Guillot, 1989). This resistance appears fatal for thousands of people each year and results in high medical and economic costs (Barton, 1998). The problem of immunity to antimicrobial agents is ubiquitous, and is partly caused by the worldwide use of antimicrobials in animal nutrition, since its addition to food formulations results in a higher efficiency (reduced feed conversion and faster growth) (Dupont & Steele, 1987) and because the use of more than half of all antimicrobial agents is associated with animal production (Aarestrup, 1999). In some countries, e.g. in the European Community, this has already led to a general prohibition of all antimicrobials used as growth enhancers in food formulations (Muirhead, 1998).

The problem with most traditional antimicrobials and other growth promoters used today is that they attack bacteria on an intracellular level (Guillot, 1989). In particular, they inhibit key enzymes involved in the synthesis of cellular building blocks. In this approach, bacteria can develop mutations in the enzymes involved or they can develop mechanisms to pump quickly the antimicrobial agents out of the cell. Alternatively they can develop enzymes that directly degrade the antimicrobial agent (e.g. β-lactamase) (Neu et al., 1980). By plasmid transfer (via microbial conjugation), resistance can be transferred quickly from one to another microbial cell (expansion of resistance) (Finland, 1971).

Since the global negative response to the use of traditional antimicrobials as growth promoters in animal nutrition, research is conducted in order to develop new types of (natural) antimicrobials or growth promoters (especially those based on an alternative method) (Mazza, 1998). The search for alternative (natural) antimicrobials is now mainly focused on the use of several (organic) acids (Eckel, 1997), new active probiotics (Chiquet & Banc Hair, 1998), prebiotics (Olsen, 1996), enzymes (Hruby & Cowieson, 2006), some plants (onion and garlic) and herb extracts (essential oils) (De Koning & Hongbiao, 1999).

Today, different types of oligosaccharides are used in various applications. WO2006/022542 describes the combined use of indigestible oligosaccharides and digestible galactose saccharides for the treatment and/or prevention of respiratory infections. WO2004/074496 describes the use of oligosaccharides consisting of galactose and glucose to develop beneficial bacteria in the gastrointestinal tract of animals. JP2002226496 describes oligosaccharides obtained by hydrolyzation of polysaccharides such as fucoidan with an anti-infective activity against *E. coli* and *Vibrio*. CN1370784 describes chitinamine oligosaccharide, which potentially can be used in cancer therapy and in the treatment of hepatosis, improving the function of the intestinal tract and in the treatment and prevention of senility. JP2002121138 describes the use of oligosaccharides from chicken egg yolks, especially sialyl-oligosaccharides, oligosaccharide-bound proteins and oligosaccharide peptides to protect the gastrointestinal tract from infection. U.S. Pat. No. 6,069,137 describes the treatment of travel diarrhoea caused by enterotoxinogenic *E. coli* by administration of oligosaccharides, containing β-galactose, covalently bonded to silica particles by a linker whereby said particles are secreted from the gastrointestinal tract. EP1018342 describes the treatment of SLT-mediated enteric infections using a solid inert affinity carrier that can be excreted from the gastrointestinal tract, on which a disaccharide is covalently bound, having affinity with SLT. U.S. Pat. No. 5,939,397 describes a method for treating cholera by administration of a 1-3 oligosaccharide, with affinity for one or more *V. cholerae* serotypes, covalently bonded through a linker to a solid, inert carrier.

Various types of MCFAs are also used in several applications. In this context, EP1294371 describes specific MCFAs as inhibitors of microbial and especially bacterial and fungal contamination and growth. In particular, EP1294371 describes the use of essential equal amounts of caprylic acid (C8) and capric acid (CIO) as antimicrobial agents, mainly active in an acidic environment like the stomach.

The aim of the present invention is to develop a feed supplement with enhanced effects on the microbial ecosystem. In particular, the present invention wants to increase the specificity and activity of feed supplements and a faster operation thereof, to improve the enteric microbial ecosystem. This invention introduces a specific combination of growth promoters which have a synergistic beneficial effect on the efficiency of animal production, feed conversion, nutrition, health and wellbeing of individuals. In this regard, the combined use of tri- and/or tetra-oligosaccharides with MCFAs can be considered as a new and innovative agent with growth stimulating properties.

SUMMARY OF THE INVENTION

In a first step, the present invention relates to a feed supplement, comprising:
- an oligomer of a carbohydrate component, preferably a homotrimer, heterotrimer, homotetramer and/or heterotetramer of a carbohydrate component, a derivative or an extract thereof, or mixtures thereof and where the said carbohydrate component is selected from the group consisting of a pentose saccharide and hexose saccharide, glucuronic and galacturonic acid, and wherein the carbohydrate components are connected by a or β bonds, and
- a medium-chain fatty acid (MCFA) or a salt or a derivative and/or mixtures thereof, whereby said MCFA is selected from the group consisting of caproic acid (C6), caprylic (C8), capric (CIO) and lauric acid (C12).

The present inventors have surprisingly demonstrated that the combined use of the oligosaccharides described above and the MCFAs described above enhances totally unexpected the efficiency of animal production on a synergistic base. This synergistic effect is manifested in different ways. Initially the described feed supplement leads to an increase of the daily growth rates of the individuals getting the feed supplement administered. The described feed supplement also provides an increase in daily food intake. The use of the described feed supplement moreover results in a decrease in mortality. Additionally this allows for a drastical reduction of the use of antibiotics.

Another advantage of the herein described feed supplements is the specific inactivation and elimination of enteropathogens, while the beneficial gastrointestinal bacterial flora is not negatively influenced.

While the herein described feed supplement gives rise to an increase of daily food intake, as well as an increase in daily weight gain, the combined use of the herein described oligosaccharides and MCFAs leads totally unexpected to an increase of efficiency by a decrease in feed conversion (a parameter determined by the ratio of daily food intake and daily weight gain) compared with the individual use of oligosaccharides and MCFAs. This means that due to the synergistic activity of the herein described feed supplement the increase in daily growth rates is unexpectedly larger than the increase in daily food intake compared with the individual use of oligosaccharides and MCFAs, resulting in an increased efficiency, and thus a reduction in feed conversion.

The synergistic effect of the herein described oligosaccharides and MCFAs combined in one feed supplement is also immuno-genetically endorsed. There where the individual administration of the said oligosaccharides and MCFAs each lead to a decreased immunological response (by an increased inactivation and excretion of the enteropathogens), the administration of a combined formulation of the oligosaccharides and MCFAs results in a synergistic decrease of the immunological activity.

The synergistic process of the said oligosaccharides and MCFAs is furthermore supported by the observation that only the combined administration brings up the effects described. In contrast, the sequential administration of the herein described oligosaccharides and MCFAs does not lead to the described synergistic effects. Moreover, the combined administration of the said oligosaccharides and MCFAs is counter-intuitive for a person skilled in the art, as MCFAs are oil-soluble, and oligosaccharides are water-soluble. The present inventors have surprisingly found that the formulating methods as described herein allows to combine incompatible constituent components, from solubility point of view, into one single composition.

Without wishing to be bound by a theory, the inventors believe that the synergistic effect of tri- and tetra-oligosaccharides and MCFAs is based on the specific way of processing of the two agents. For instance specific enteropathogens as Enterobacteriaceae are eliminated by MCFAs in the stomach (which is an acidic environment) and in the proximal part of the small intestine (which is a slightly acidic environment) and in the gastrointestinal tract followed by a selective agglutination and secretion of the surviving and/or resistant enteropathogens through tri- and tetra-oligosaccharides, while also adhesion to the intestinal wall is prevented. Such combined synergistic effects of other types of growth promoters for use in cattle breeding has never been described before. The complementary way of working of the described oligosaccharides and MCFAs leads totally unexpected to a synergistic effect on the efficiency of animal production. Such a synergistic effect is even more unexpected due to the different mechanism of the described oligosaccharides and MCFAs, on one hand a specific inactivation of enteropathogens in the acidic environment of the stomach by the said MCFAs and on the other hand the specific agglutination and secretion of enteropathogens in the gastrointestinal tract by the said tri- and tetra-oligosaccharides. One would expect that such decoupled processing mechanisms, where no functional interaction occurs between the components of the feed supplement described herein, would not lead to the synergistic effect described herein.

In another aspect, the present invention relates to a food comprising a feed supplement as described herein.

In a further aspect the present invention relates to the use of a feed supplement or a food as described herein for the preparation of a composition in order to:
- improve the microbial ecosystem in the gastrointestinal tract of an animal,
- control and regulate selectively the enteropathogens in the gastrointestinal tract of an animal,
- optimize the microbial colonization of the gastrointestinal tract by inhibition and agglutination of specific enteropathogens,
- improve weight gain, to reduce feed conversion and to improve nutritive value, health and wellbeing of an animal, and/or
- stimulate specific growth in cattle breeding.

The present invention also relates to a method for obtaining the above effects through administration of said the food or feed supplement.

DESCRIPTION OF FIGURES

FIG. 1A shows agglutination of the pathogen *Brachyspira hyodysenteriae* by tri and/or tetra-manno-oligo-saccharides. FIG. 1B shows that the non-pathogenic *Lactobacillus amylovorus* is not agglutinated.

DETAILED DESCRIPTION OF THE INVENTION

Figure 1B:
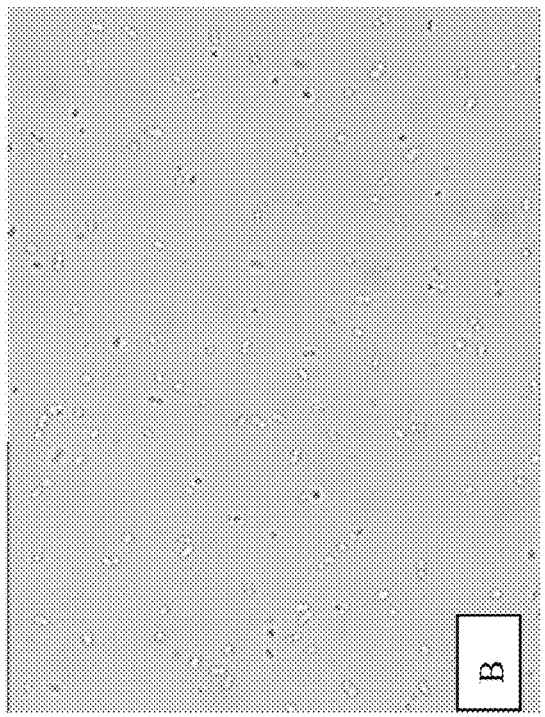
FIGS. 1A and 1B: Agglutination by tri and/or tetra-manno-oligo-saccharides of A) pathogen *Brachyspira hyodysenteriae*, but not of B) non-pathogenic *Lactobacillus amylovorus*.

The present invention relates to a feed supplement to improve the microbial ecosystem in the gastrointestinal tract so that the efficiency of livestock production is improved, in particular, daily weight gain, feed conversion, nutritive value, health and wellbeing of animals while the feed supplement includes:

- an oligomer of a carbohydrate component, preferably a homotrimer, heterotrimer, homotetramer and/or heterotetramer of a carbohydrate component, or a derivative thereof or an extract thereof, or mixtures thereof and where the said carbohydrate component is selected from the group consisting of a pentose saccharide, hexose saccharide, glucuronic and galacturonic acid, and wherein the carbohydrate-components are connected by a or β bonds, and
- a medium-chain fatty acid (MCFA) or a salt or a derivative and/or mixtures thereof and where the so called MCFA is selected from the group consisting of caproic acid (C6), caprylic (C8), capric (CIO) and lauric acid (C12).

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

A "feed supplement" refers to a substance, formulation or composition added in small quantities to an edible composition (such as food or a nutrient which can be eaten by animals and/or human beings) to improve this edible composition. This improvement means that the edible composition has a beneficial effect on the individual consuming this. Such beneficial effect can be determined by parameters such as weight gain, food intake, feed conversion, infection pressure and/or degree, animal wellbeing, animal health, and the like. Feed supplement means that it is suitable for consumption by animals or human beings. In a preferred embodiment, the feed supplement of the invention described herein enables to decrease the amount of gastrointestinal microbial pathogens by over 25%, preferably more than 50%, more preferably more than 75% and most preferably to 100%.

An "oligomer of a carbohydrate component" refers to an oligosaccharide. Oligosaccharides which can be used according to the invention comprise at least two saccharide monomers bonded covalently by a or β bonds or a combination of a and β bonds. Following the invention. L or D isomers of oligosaccharides can be used. The saccharide monomers can be aldoses or ketoses, occurring in an acyclic or a cyclic form. The cyclic forms of the saccharide monomers can occur as a or β isomers depending on the position of the OH-group of the anomeric carbon. The L or D isomers of the acyclic form of the saccharide monomers can be used. The term "oligosaccharides" is known by the skilled person and means short chains of covalently bonded saccharides (or sugar or carbohydrate) monomers. The oligosaccharides which can be used following the invention include 2, 3, 4, 5, 6, 7, 8, 9, 10 or more saccharide monomers. The oligosaccharides can have a branched or unbranched form. As herein described, "branched" means that the oligosaccharide contains at least one monosaccharide residue linked to more than two other monosaccharide residues whereby at least one of the linked monosaccharide residues is not positioned in the longitudinal direction of the oligosaccharide. The inventors have demonstrated that pathogens are preferably agglutinated by tri- and/or tetra-oligosaccharides. Therefore, in a preferred embodiment, the oligosaccharides consist of three or four saccharide monomers. Following the invention, the embodiment of the oligosaccharides are homotrimers, heterotrimers, homotetramers or heterotetramers. The homo-oligomers (homomeres) are composed of identical saccharide monomers, where the hetero-oligomers (heteromeres) are composed of different saccharide monomers, especially 2, 3, 4 or more different saccharide monomers. The advantage of the oligosaccharides described herein is that they can be used without providing them with an (inert) carrier. Moreover, the oligosaccharides described herein only have a selective effect on enteropathogens and not on the non-pathogenic gastrointestinal microflora.

In one embodiment, the derivates, extracts and/or mixtures of the said oligosaccharides can be used in the feed supplement. The term "derivatives" is defined as modified oligosaccharides. As an example but without limitation, derivatives are oxidized or substituted forms of oligosaccharides. For instance, oxidation of the saccharide monomer components of an oligosaccharide in which the saccharide monomer is galactose will result in the formation of galacturonic acid. Following the invention, "extracts" means that the oligosaccharides can be provided as an extract or (purified) concentrate of oligosaccharide containing compositions.

In one embodiment, the invention describes a feed supplement, wherein the pentose saccharides are selected from the group consisting of ribose, arabinose, xylose and lyxose. In another embodiment, the invention describes a feed supplement, wherein the hexose saccharides are selected from the group consisting of allose, altrose, gulose, idose, talose, mannose.

As described herein, the term "carbohydrate" refers to an organic compound consisting of carbon, hydrogen and oxygen atoms. This term therefore comprises but is not limited to organic compounds such as monosaccharides, disaccharides or carboxylic acids such as lactic acid, gluconic acid and glucoronic acid.

In a further embodiment, the invention describes a feed supplement, wherein the MCFA is provided as a free MCFA, as a mono-, di- and/or tri-glyceride of the said MCFA and/or a $NH^{4+}$—, $Na^+$—, $K^+$— and/or $Ca^{2+}$— salt of this MCFA. The two fatty acids bonded to the glycerol by an ester linkage in the diglyceride may be the same or may be different fatty acids. The three fatty acids bonded to the glycerol by an ester linkage in the triglyceride may all three be the same or may be three different fatty acids or any combination of two of the same fatty acids and one different fatty acid. As described herein, the term "medium chain fatty acids" or "MCFA" refers to fatty acids with a medium chain length and wherein the fatty acids may be saturated or unsaturated. The unsaturated fatty acids may contain either cis- or transconfigurations. According to the invention, the MCFAs comprise from 6 to 12 carbon atoms, especially caproic (C6), caprylic (C8), capric (CIO) or lauric acid (C12). In one embodiment, salts, derivatives and/or mixtures of the herein described MCFAs are used in the feed supplement as described herein following the invention. The use of salts prevents the spread of odors, which may occur when using the free fatty acids. As described herein, the term "derivative of a MCFA" refers to a MCFA wherein the carboxyl group is reversible converted to another group (excluding salts), preferably but without limitation, to an amide, ester or glyceride. As described herein, the term "free MCFA" refers to a MCFA not been converted into a salt or a derivative (such as an amide, ester or glyceride). As used herein, the term "MCFA salt" refers to a salt of the fatty acid.

In one embodiment, the MCFAs are chemically modified and they are provided with side chains, including, but without limitation, one or more alkyl groups, preferably C1-C10 alkyl, particularly methyl or ethyl groups.

In one embodiment and following the invention, the feed supplement contains additional raw materials (additives) and/or growth-promoting substances as described herein. In a preferred embodiment, the additives are selected from the group consisting of flavorings and herb extracts. In a further preferred embodiment, the growth-promoting ingredients are selected from the group consisting of antibiotics, probiotics, prebiotics, essential oils, enzymes, fatty acids and (in)organic acids. Non-limiting examples of organic acids which can be used in one embodiment of the invention include C1-C12 carboxylic acids, particularly non-substituted carboxylic acids such as formic acid, acetic acid, propionic acid, butyric acid and valeric acid; and/or substituted carboxylic acids such as adipic acid, maleic, succinyl acid, citric acid, fumaric acid, tartaric acid, including cyclic carboxylic acids such as picolinic acid. The organic acids may be one or more substituted or unsubstituted carboxylic acids as well as mixtures thereof, as well as saturated, unsaturated, cyclic and/or aliphatic carboxylic acids or mixtures thereof, as well as metal complexes and/or salts thereof, as well as racemic and/or enantiomeric forms thereof. Non-limiting examples of inorganic acids which can be used in one embodiment of the invention include strong acids in small quantities, such as perchloric acid (hydrogen perchlorate), hydrogen iodide, hydrogen bromide (hydrobromic acid), hydrogen chloride (hydrochloric acid), sulfuric and nitric acids as well as weak inorganic acids such as phosphoric acid, hydrofluoric acid, hypochlorous acid and nitrous acid.

In one embodiment and according to the invention, the oligosaccharides in the feed supplement are present in liquid or solid form. In another embodiment and according to the invention, the MCFAs in the feed supplement are present in liquid or solid form. In a further embodiment, the feed supplement is formulated, according to the invention, as a liquid or solid form. The term "solid" is specifically defined as a powder. The term "liquid" is specifically defined as an aqueous solution or a solution in oil. The oligosaccharides as described according to the invention are water soluble and can be provided as powder and as an aqueous solution. The MCFAs as described herein according to the invention are oil soluble and can be provided as powder and as an oil solution. Caproic acid is also water soluble and can therefore also be provided as an aqueous solution. The feed supplement as described herein can include an oligosaccharide-powder and a MCFA powder, an oligosaccharide powder and a MCFA-oil solution, an oligosaccharide-aqueous solution and an MCFA-powder, an oligosaccharide-aqueous solution and an MCFA oil solution (which creates an emulsion), or an oligosaccharide-aqueous solution and an MCFA-aqueous solution (in case the MCFA is caproic acid).

In one embodiment, the concentration of the oligosaccharides as described herein are at least 1, 5, 10, 15, 20, 25, 30, 35, 40, 45, 50, 55, 60, 65, 70, 75, 80, 85, 90, 95, 99% by weight of the feed supplement. In another embodiment, the concentration of the MCFAs as described herein are at least 1, 5, 10, 15, 20, 25, 30, 35, 40, 45, 50, 55, 60, 65, 70, 75, 80, 85, 90, 95, 99% by weight of the feed supplement. In a further embodiment, the quantity of the oligosaccharides as described herein (based on dry weight) is between 1 g/100 g feed supplement (1% by weight) and 50 g/100 g feed supplement (50% by weight), preferably 25 g/100 g feed supplement (25% by weight). In a further embodiment, the amount of MCFAs as described herein (based on dry weight) is between 1 g/100 g feed supplement (1% by weight) and 70 g/100 g feed supplement (70% by weight), preferably 35 g/100 g feed supplement (35% by weight). This means that the concentration of the combined formulation of the MCFAs and the oligosaccharides as described herein is maximal equal to 100% by weight of the feed supplement.

The present invention also relates to an edible composition, particularly a dietary (product), food or food composition comprising the feed supplement as described herein.

In one embodiment, according to the invention and as described herein the food contains up to 1% by weight of oligosaccharides (or extracts, derivatives or mixtures). In a further embodiment, according to the invention and as described herein the food contains up to 10% by weight of the MCFAs (or salts, derivatives, or mixtures). In a further embodiment, the food contains an amount of oligosaccharides (or extracts, derivatives or mixtures) as described herein (based on dry weight) between 0.01 g/100 g food (0.01% by weight) and 2 g/100 g food (2% by weight), preferably 0.05 g/100 g food (0.05% by weight). In a further embodiment, the food contains an amount of MCFAs (or salts, derivatives, or mixtures) as described herein (based on dry weight) between 0.01 g/100 g food (0.01% by weight) and 1 g/100 g food (1% by weight), preferably 0.07 g/100 g food (0.07% by weight).

Following the invention and as described herein, the feed supplement or the feed can be used to control, regulate and/or specifically eliminate enteropathogens in the gastrointestinal tract of animals or human beings. The feed supplement or feed causes an improvement in the microbial ecosystem in the gastrointestinal tract by the dual and synergistic effect of oligosaccharides and MCFAs as described herein. During this process, the enteropathogens are not only eliminated, they are also agglutinated and excreted from the body and thus the toxic effects of killed pathogens are minimized. An additional advantage of the present invention is that only the enteropathogens are eliminated and removed, there where the positive or non-pathogenic gastrointestinal microbial flora (e.g. *Lactobacillus*) is maintained. "(Entero)pathogens", as opposed to "favorable or non-pathogenic gastrointestinal microbial flora" is herein defined as micro-organisms which have an adverse effect on the host, particularly those who cause diseases or disorders. Other forms of adverse effects are reduced daily food intake, reduced daily weight gain, increased feed conversion, and in general a reduced health and wellbeing.

In one embodiment, according to the invention and as described herein, the feed supplement or feed can be used to selectively eliminate, suppress or regulate one or more enteropathogens, selected from the group consisting of filamentous micro-organisms and micro-organisms with adhesion structures. Gram negative bacteria, Gram positive bacteria, fungi, yeasts and viruses.

In a further embodiment, the enteropathogens are selected from the group consisting of the bacterial pathogens of the genera *Brachispira, Vibrio, Escherichia, Salmonella* (including, without limitation *Salmonella typhimurium, Salmonella enteritidis* and *Salmonella java*), *Shigella, Klebsiella, Erwinia, Yersinia, Campylobacter* (including, without limitation. *Campylobacter jejuni, Campylobacter coli, Campylobacter laris*, and *Campylobacter upsaliensis*), *Helicobacter, Pseudomonas, Enterococcus* and *Clostridium*; preferably *Brachyspira hyodysenteriae*; yeast and fungal pathogens of the genera *Penicillium, Aspergillus, Fusarium, Cephalosporum, Saccharomyces, Candida, Fungi imperfecti* and *Hemiascomycetes*; and viral pathogens of the genera Norovirus and Rotavirus.

In one aspect, the present invention relates to a method in order to inhibit, eliminate, excrete, demise, regulate and/or control the above enteropathogens through the administration of the feed supplement or the feed as described herein according to the invention. In a further aspect the present invention relates to a method in order to increase the health of an individual, the daily weight gain and the daily food intake and to increase the feed conversion, and in general to increase the wellbeing by administration of the feed supplement or the feed as described herein according to the invention.

In one embodiment, according to the invention and as described herein, the feed supplement or feed, is administered to animals which are selected from the group consisting of fish, amphibians, reptiles, birds and mammals, including, without limitation, adult or juvenile ruminants, sheep, goats, cattle, pigs, horses, poultry, fowls, animals (e.g. dogs, cats, rabbits, hamsters, guinea pigs), and preferably selected from the group consisting of poultry, pigs, ruminants and human beings.

The invention is further described by the following non-limiting examples which further illustrate the invention, and are not intended to, nor should they be interpreted to, limit the scope of the invention.

It is supposed that the present invention is not restricted to any form of realization described previously and that some modifications can be added to the presented example of fabrication without reappraisal of the appended claims.

EXAMPLES

Experiment 1: Effect of a Mixture of Tri/Tetra-Galacturon-Oligosaccharides and MCFAs on the Efficiency of Pigs 3×147 piglets were fed with following feed:
(1) control feed supplemented with 0.05% by weight tri/tetra-galacturon-oligosaccharides;
(2) control feed supplemented with 0.07% by weight MCFAs, and
(3) control feed supplemented with a mixture of 0.05% by weight tri/tetra-galacturon-oligosaccharides and 0.07% by weight MCFAs.

The control feed was a meal composed of materials suitable for animal feed. Water was provided ad libitum.

During this experiment daily weight gain, daily food intake, feed conversion and mortality were assessed after 3 weeks. The results are summarized in Table 1.

The MCFAs used were C6-C12 MCFAs.

TABLE 1

| Feed | (1) | (2) | (3) |
|---|---|---|---|
| Weight gain | 170.5 ± 61.3 | 177.3 ± 61.4 | 191.2 ± 60.6 |
| Food intake | 249.1 ± 19.9 | 259.9 ± 20.3 | 270.3 ± 46.9 |
| Feed conversion | 1.46 ± 0.10 | 1.47 ± 0.12 | 1.42 ± 0.08 |
| Mortality | 5/147 | 3/147 | 0/147 |

Table 1 shows that the combined use of tri/tetra-galacturon-oligosaccharides and MCFAs results in improved zootechnical parameters, such as daily weight gain, daily food intake, feed conversion and mortality as an indicator of the health status of piglets. The combined use of tri/tetra-oligosaccharides and MCFAs acts synergistically to improve the efficiency and health status.

Additional to this it was demonstrated that the sequential administration of tri/tetra-oligosaccharides and MCFAs (defined as a frequency>1 day) did not resulted in the demonstrated synergistic effect of a simultaneous administration (data not shown).

Experiment 2: Effect of a Mixture of Tri/Tetra-Manno-Oligosaccharides and MCFAs on the Efficiency of Infected Chickens Under Pressure Male broilers (ROSS 308) were used in this experiment. The chickens were orally infected with *Campylobacter jejuni* (CAMP/VFU 612/21, immune to erythromycin, 106 CFU/ml). This pathogen allows assessing the health status of the chickens through the determination of acute phase proteins.

The total number of chickens in this experiment was 48, divided into four groups of 12 chickens each. The following feeds were administered to the chickens:
(1) control feed supplemented with 0.05% by weight tri/tetra-manno-oligo-saccharides;
(2) control feed supplemented with 0.07% by weight MCFAs;
(3) control feed supplemented with a mixture of 0.05% by weight tri/tetra-manno-oligosaccharides and 0.07% by weight MCFAs, and
(4) control feed alone.

The control feed was a herd composed of materials suitable for use as chicken feed. Water and feed were provided ad libitum.

In this example, the health status of the chickens was evaluated by the amount of acute phase proteins (APP) in the blood. The results are shown in Table 2.

The MCFAs used were C6-C12 MCFAs.

TABLE 2

| Feed | (1) | (2) | (3) | (4) |
|---|---|---|---|---|
| APP (mg/l) | 349 | 356 | 305 | 391 |

Table 2 shows that feed supplemented with a mixture of tri/tetra-manno-oligosaccharides and MCFAs are able to improve the health status of chickens. The combined use of tri/tetra-oligosaccharides and MCFAs acts synergistically to improve the health status.

In additional to this, it was shown that the sequential administration of tri/tetra-oligosaccharides and MCFAs (defined as a frequency>1 day) did not result in the demonstrated synergistic effect of simultaneous administration (data not shown).

Experiment 3: Selective Effect of Tri/Tetra-Manno-Oligosaccharides on Pathogenic Agglutination Tri- and/or tetra-manno-oligosaccharides were incubated in a liquid in a dose of 0.07% at pH 7.0 (conditions of the small intestine) with (filamentous) *Brachyspira hyodysenteriae* and *Lactobacillus amylovorus* cells for 10 minutes. After 10 minutes agglutination was visualized by microscopic analysis. The results are shown in FIG. 1.

Figure 1A:
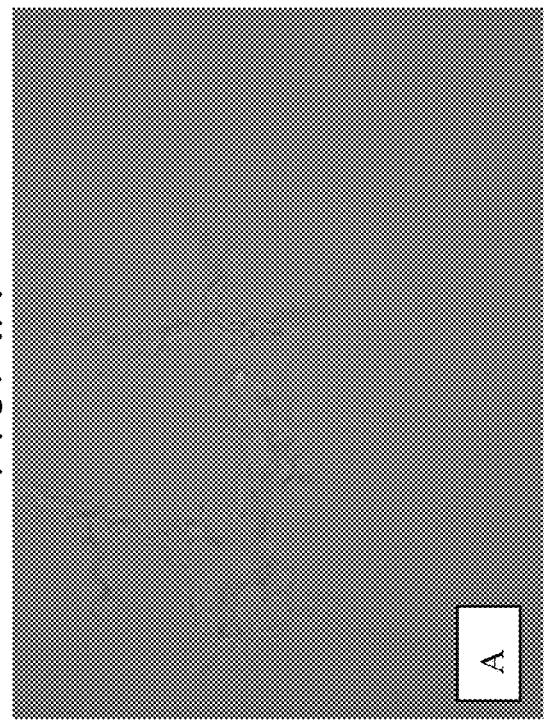

FIG. 1 shows that tri and/or tetra-manno-oligo-saccharides are capable to agglutinate *Brachyspira hyodysenteriae* cells (a model enteropathogen). In contradiction to this, tri and/or tetra-manno-oligo-saccharides are unable to agglutinate *Lactobacillus amylovorus* cells (a positive model bacteria). Tri and tetra-oligosaccharides specifically agglutinate pathogenic microorganisms.

What is claimed is:

1. A method for selectively eliminating, suppressing or regulating one or more enteropathogens in an animal, wherein the enteropathogen is a virus, comprising administering a feed supplement to the animal comprising:
    a homotrimer, heterotrimer, homotetramer and/or heterotetramer of a carbohydrate component, or a derivative thereof or an extract thereof, or mixtures thereof, whereby said carbohydrate component is selected from the group consisting of a pentose saccharide, a hexose saccharide, glucuronic and galacturonic acid, and wherein the carbohydrate-components are connected by means of α and/or β bonds; and
    a medium-chain fatty acid (MCFA) or a salt or a derivative and/or mixtures thereof, whereby said MCFA is selected from the group consisting of caproic acid (C6), caprylic acid (C8), capric acid (C10) and lauric acid (C12); and
measuring viral infection pressure or degree in the animal.

2. The method of claim 1, wherein the viral pathogen is decreased by more than 25%.

3. The method according to claim 1, wherein the pentose saccharides are selected from the group consisting of ribose, arabinose, xylose and lyxose.

4. The method according to claim 1, wherein the hexose saccharides are selected from the group consisting of allose, altrose, gulose, idose, talose and mannose.

5. The method according to claim 1, with the MCFA provided as a free MCFA, as a mono-, di- and/or tri-glyceride of the said MCFA and/or a $NH_4^+$—, $Na^+$—, $K^+$— and/or $Ca^{2+}$— salt of said MCFA.

6. The method according to claim 1, wherein the feed supplement further comprises raw materials and/or growth-promoting substances.

7. The method according to claim 6, wherein the raw materials are selected from the group consisting of aromas and plant extracts, and wherein growth-promoting ingredients are selected from the group consisting of antibiotics, probiotics, prebiotics, essential oils, enzymes, fatty acids and organic acids.

8. The method according to claim 1, wherein said homotrimer, heterotrimer, homotetramer and/or heterotetramer of the said carbohydrate components are present in liquid or solid phase, whereby said MCFA are present in liquid or solid phase, and wherein the feed supplement is present in liquid or solid phase.

9. The method according to claim 1, wherein the homotrimer, heterotrimer, homotetramer and/or heterotetramer of the said carbohydrate component or the MCFA are present in the feed supplement in an amount of at least 1, 5, 10, 15, 20, 25, 30, 35, 40, 45, 50, 55, 60, 65, 70, 75, 80, 85, 90, 95, 99% by weight of the feed supplement.

10. The method according to claim 1, wherein the homotrimer, heterotrimer, homotetramer and/or heterotetramer of the said carbohydrate component are administered at a dose of between 1 g/100 g feed supplement (1% by dry weight) and 50 g/100 g feed supplement (50% by dry weight), preferably 25 g/100 g feed supplement (25% by dry weight), and wherein
    the MCFA are administered at a dose of between 1 g/100 g feed supplement (1% by dry weight) and 70 g/100 g feed supplement (70% by dry weight), preferably 35 g/100 g feed supplement (35% by dry weight).

11. The method of claim 1, whereby viral enteropathogens in the gastrointestinal tract of the animal are specifically inhibited or agglutinated.

12. The method of claim 1, wherein the viral enteropathogens comprise a rotavirus or norovirus.

13. The method according to claim 1, wherein the animal is selected from the group consisting of fish, amphibians, reptiles, birds mammals, and preferably is selected from the group consisting of poultry, pigs, ruminants and humans.

14. The method of claim 1, wherein the feed supplement is administered in animal feed.

15. The method of claim 1, further comprising mixing the feed supplement with animal feed before administering to the animal.

16. The method according to claim 1, wherein the feed supplement is not an emulsion.

* * * * *